United States Patent
Govari et al.

(10) Patent No.: US 8,260,400 B2
(45) Date of Patent: Sep. 4, 2012

(54) MODEL-BASED CORRECTION OF POSITION MEASUREMENTS

(75) Inventors: Assaf Govari, Haifa (IL); Andres Claudio Altmann, Haifa (IL); Yaron Ephrath, Karkur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 13/100,369

(22) Filed: May 4, 2011

(65) Prior Publication Data

US 2011/0213240 A1    Sep. 1, 2011

(51) Int. Cl.
*A61B 5/05*    (2006.01)
(52) U.S. Cl. .......... 600/424; 600/547; 607/2; 607/8
(58) Field of Classification Search .......... 600/424, 600/547; 607/2, 8
See application file for complete search history.

(56) References Cited

U.S. PATENT DOCUMENTS

| | | | |
|---|---|---|---|
| 5,899,860 A | 5/1999 | Pfeiffer et al. | |
| 5,983,126 A | 11/1999 | Wittkampf | |
| 6,129,668 A * | 10/2000 | Haynor et al. | 600/424 |
| 6,773,393 B1 | 8/2004 | Taniguchi et al. | |
| 7,640,106 B1 * | 12/2009 | Stokar et al. | 701/214 |
| 2005/0107687 A1 | 5/2005 | Anderson | |
| 2006/0173289 A1 * | 8/2006 | Aizawa et al. | 600/424 |
| 2006/0247520 A1 * | 11/2006 | McGee | 600/434 |
| 2007/0038078 A1 * | 2/2007 | Osadchy | 600/424 |

FOREIGN PATENT DOCUMENTS
WO    WO 01/46577 A    6/2001

* cited by examiner

*Primary Examiner* — James Kish
(74) *Attorney, Agent, or Firm* — Louis J. Capezzuto

(57) ABSTRACT

Visualization of a probe when impedance-based measurement technology is being used is improved by stabilizing a displayed image of the probe or catheter. Using a model of reasonable probe shapes and a matching algorithm, an erroneous probe image is adjusted so that it assumes a realistic shape on a display. A range of positional variations is also incorporated in the model. When an apparent probe position exceeds a permissible range of motion, the probe image is constrained to a realistic position.

10 Claims, 5 Drawing Sheets

MODEL-BASED CORRECTION OF POSITION MEASUREMENTS

BACKGROUND OF THE INVENTION

1. Field of the Invention

This invention relates to sensing the position of an object placed within a living body. More particularly, this invention relates to detection and compensation for artifacts experienced during position sensing of a probe in a living body.

2. Description of the Related Art

A wide range of medical procedures involve placing objects, such as sensors, tubes, catheters, dispensing devices, and implants, within the body. Realtime imaging methods are often used to assist doctors in visualizing the object and its surroundings during these procedures. In most situations, however, realtime three-dimensional imaging is not possible or desirable. Instead, systems for obtaining realtime spatial coordinates of the internal object are often utilized.

Many such position sensing systems have been developed or envisioned in the prior art. Some systems involve attaching sensors to the internal object in the form of transducers or antennas, which can sense magnetic, electric, or ultrasonic fields generated outside of the body. For example, U.S. Pat. No. 5,983,126 to Wittkampf, whose disclosure is incorporated herein by reference, describes a system in which three substantially orthogonal alternating signals are applied through the subject. A catheter is equipped with at least one measuring electrode, and a voltage is sensed between the catheter tip and a reference electrode. The voltage signal has components corresponding to the three orthogonal applied current signals, from which calculations are made for determination of the three-dimensional location of the catheter tip within the body. Similar methods for sensing voltage differentials between electrodes are proposed by U.S. Pat. No. 5,899,860 to Pfeiffer, whose disclosure is incorporated herein by reference. In both of these systems, it is necessary to undertake a separate calibration procedure in order to adjust for discrepancies between the apparent position of the catheter tip as measured and its actual position.

SUMMARY OF THE INVENTION

Using impedance measurement technology for determining the position of a probe or catheter, it has been found that if the probe image is not constrained to assume realistic shapes and positions, sudden fluctuations can occur, which are disconcerting to the physician who is viewing the patient monitor. According to disclosed embodiments of the invention, visualization of a probe when impedance-based measurement technology is being used is improved by stabilizing a displayed image of the probe or catheter. The invention is useful in voltage-based impedance systems, e.g., the non-contact mapping system produced by Endocardial Solutions Inc. (ESI), St. Paul, Minn., as well as current-based systems, such as that described in U.S. patent application Ser. No. 11/030,934, filed Jan. 7, 2005, which is assigned to the assignee of the present patent application and whose disclosure is incorporated herein by reference. Embodiments of the present invention may also be used in position measurement systems based on other principles.

In one aspect of the invention, a model describing reasonable probe shapes is created. Typically, a probe, such as a catheter tip, is flexible, and can therefore assume a range of curved shapes. The measured position and conformation of a probe is correlated with the model, and a matching algorithm is used to determine if the probe image has a realistic shape, in accordance with the model topology. The probe image is adjusted as necessary to force it into constraints defined by the model.

According to another aspect of the invention, a probe inside the body can be assumed to move no faster than a certain speed. If an impedance fluctuation causes an apparent movement that would exceed this maximum speed, the probe image can be constrained to a position bounded by the maximum speed.

In another aspect of the invention, a Kalman filter is employed for prediction of probe positions and shapes based on prior measurements. A shape model including variations and statistics regarding the errors in the model may be employed in the estimation process, using model-specific Kalman equations. For example, variation of the deflection of a shaft and the likelihood of finding a shaft having a given curvature can be included into the shape estimation of the model.

An embodiment of the invention provides a method of determining a position of a probe that has been inserted into a body of a subject, which is carried out by determining an apparent position of the probe in the body, establishing that a first displacement between the apparent position and a prior position of the probe at a known time corresponds to a first rate of motion that exceeds a predetermined limit, adjusting the apparent position to a new position such that a second displacement between the new position and the prior position corresponds to a second rate of motion that is less than the predetermined limit, and displaying the new position.

According to an aspect of the method, the apparent position is determined by measuring impedance between the probe and a plurality of locations that are remote from the probe.

According to a further aspect of the method, measuring the impedance, which is carried out by passing electrical currents through the body between at least one electrode disposed on the probe and the plurality of locations, and measuring respective characteristics of currents passing through the plurality of the locations.

In an additional aspect of the method, adjusting the apparent position is performed using a Kalman filter.

An embodiment of the invention provides a method of determining a position of a probe that has been inserted into a body of a subject, which is carried out by maintaining a model of topologies, including a range of shapes assumable by the probe, determining an apparent conformation of the probe in the body, establishing that the apparent conformation is outside the range, referencing the model to determine a true conformation of the probe, adjusting the apparent conformation to the true conformation and displaying the true conformation.

Yet another aspect of the method includes adjusting an apparent position of the probe to a true position responsively to referencing the model.

An embodiment of the invention provides an apparatus for sensing the position of a probe having at least one probe electrode, the probe being adapted to be inserted into a body of a subject. The apparatus includes a plurality of body surface electrodes, which are adapted to be fixed to a surface of the body at respective locations, a display, and a controller, which is adapted to be coupled to the probe and to the body surface electrodes so as to pass electrical currents through the body between the probe electrode and the body surface electrodes. The controller is operative to determine position coordinates of the probe by measuring respective characteristics of the currents passing through the body surface electrodes. The controller is operative for determining an apparent position of the probe in the body, establishing that a first displacement between the apparent position and a prior position of the probe at a known time corresponds to a first rate of motion that exceeds a predetermined limit, adjusting the apparent position to a new position such that a second displacement between the new position and the prior position corresponds to a second rate of motion that is less than the predetermined limit, and displaying the new position on the display.

An embodiment of the invention provides an apparatus for sensing the position of a probe having a plurality of probe electrodes, the probe being adapted to be inserted into a body of a subject. The apparatus includes a plurality of body surface electrodes, which are adapted to be fixed to a surface of the body at respective locations, a display, and a controller, which is coupled to the probe and to the body surface electrodes. The controller transmits electrical currents through the body between the probe electrodes and the body surface electrodes, and is adapted to determine position coordinates of the probe by measuring respective characteristics of the currents passing through the body surface electrodes. The controller maintains a model of topologies including a range of shapes assumable by the probe, determines an apparent conformation of the probe in the body, establishes that the apparent conformation is outside the range, referencing the model to determine a true conformation of the probe, aligns the apparent conformation to the true conformation and displays the true conformation.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

System Overview

Figure 1:
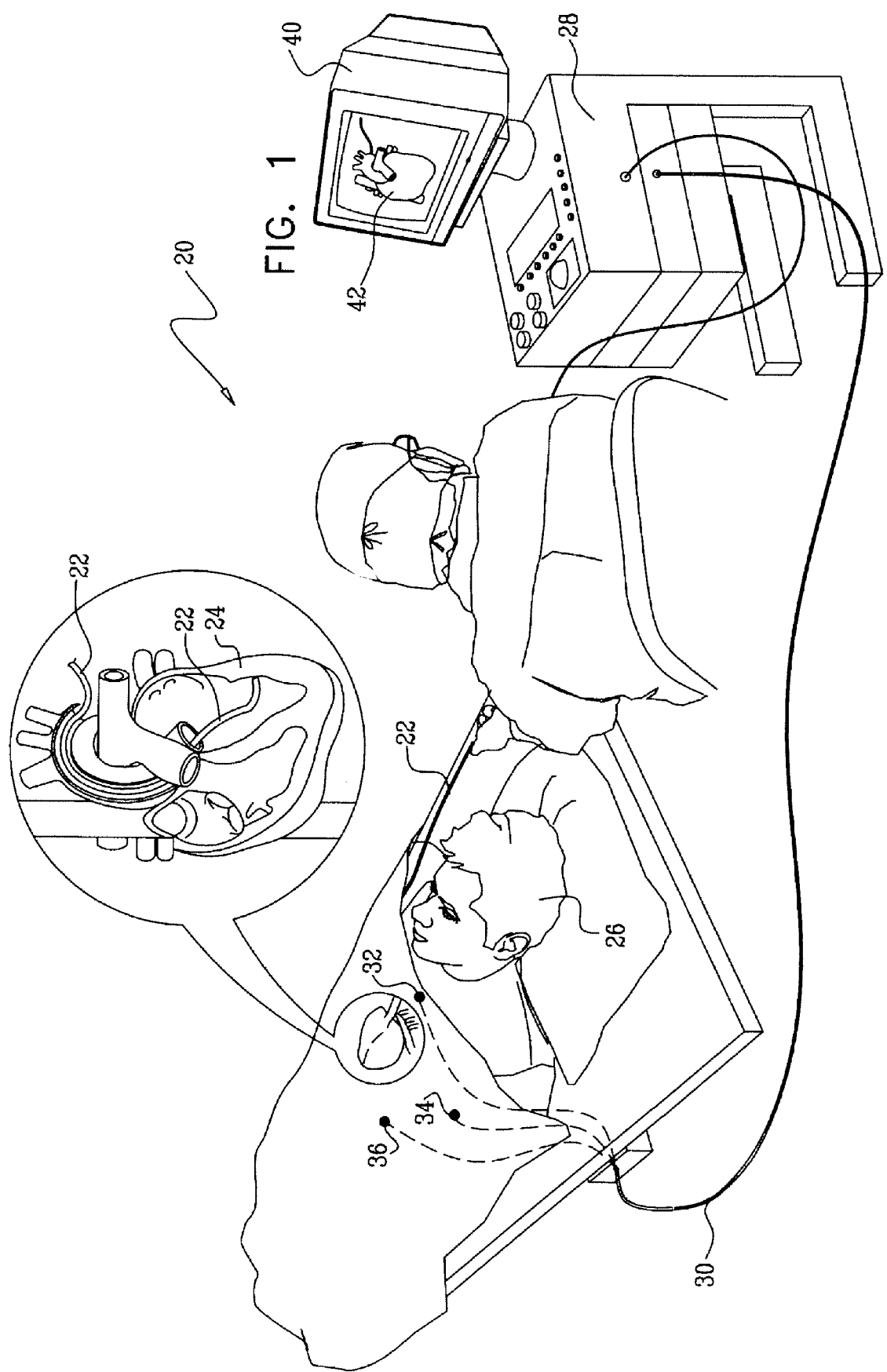
FIG. 1 is an illustration of a position sensing system, which is constructed and operative in accordance with a disclosed embodiment of the invention.

Turning now to the drawings, reference is initially made to FIG. 1, which is an illustration of a position sensing system 20, which is constructed and operative in accordance with a disclosed embodiment of the invention. The system 20 is used in determining the position of a probe, such as a catheter 22, which is inserted into an internal body cavity, such as a chamber of a heart 24 in a subject 26. Typically, the catheter is used for diagnostic or therapeutic treatment, such as mapping electrical potentials in the heart or performing ablation of heart tissue. The catheter or other intrabody device may alternatively be used for other purposes, by itself or in conjunction with other treatment devices. The distal tip of the catheter 22 comprises one or more electrodes, described below. These electrodes are connected by wires through the insertion tube of the catheter 22 to driver circuitry in a control unit 28, as described below. The control unit is connected by wires through a cable 30 to body surface electrodes, which typically comprise adhesive skin patches 32, 34, 36. In alternative embodiments of the invention, the electrodes on the body surface may vary in number and may take other forms, such as subcutaneous probes or a handheld device operated by a medical professional 38. The patches 32, 34, 36 may be placed at any convenient locations on the body surface in the vicinity of the probe. For example, for cardiac applications, the patches 32, 34, 36 are typically placed around the chest of the subject 26. There is no special requirement regarding the orientation of patches relative to each other or to the coordinates of the body, although greater accuracy may be achieved if the patches are spaced apart, rather than clustered in one location. There is no requirement that the placement of the patches be along fixed axes. Consequently, patch placement can be determined in order to interfere as little as possible with the medical procedure being performed. The control unit 28 determines position coordinates of the catheter 22 inside the heart 24 based on the impedance measured between the catheter 22 and the patches 32, 34, 36. The control unit 28 drives a display 40, which shows the catheter position inside the body. The catheter 22 may be used in generating a map 42 of the heart, for example, an electrical map, wherein the electrodes on the catheter are used alternately for position sensing and for measuring electrical potentials generated in the heart tissue. The catheter position may be superimposed on this map or on another image of the heart.

Figure 2:
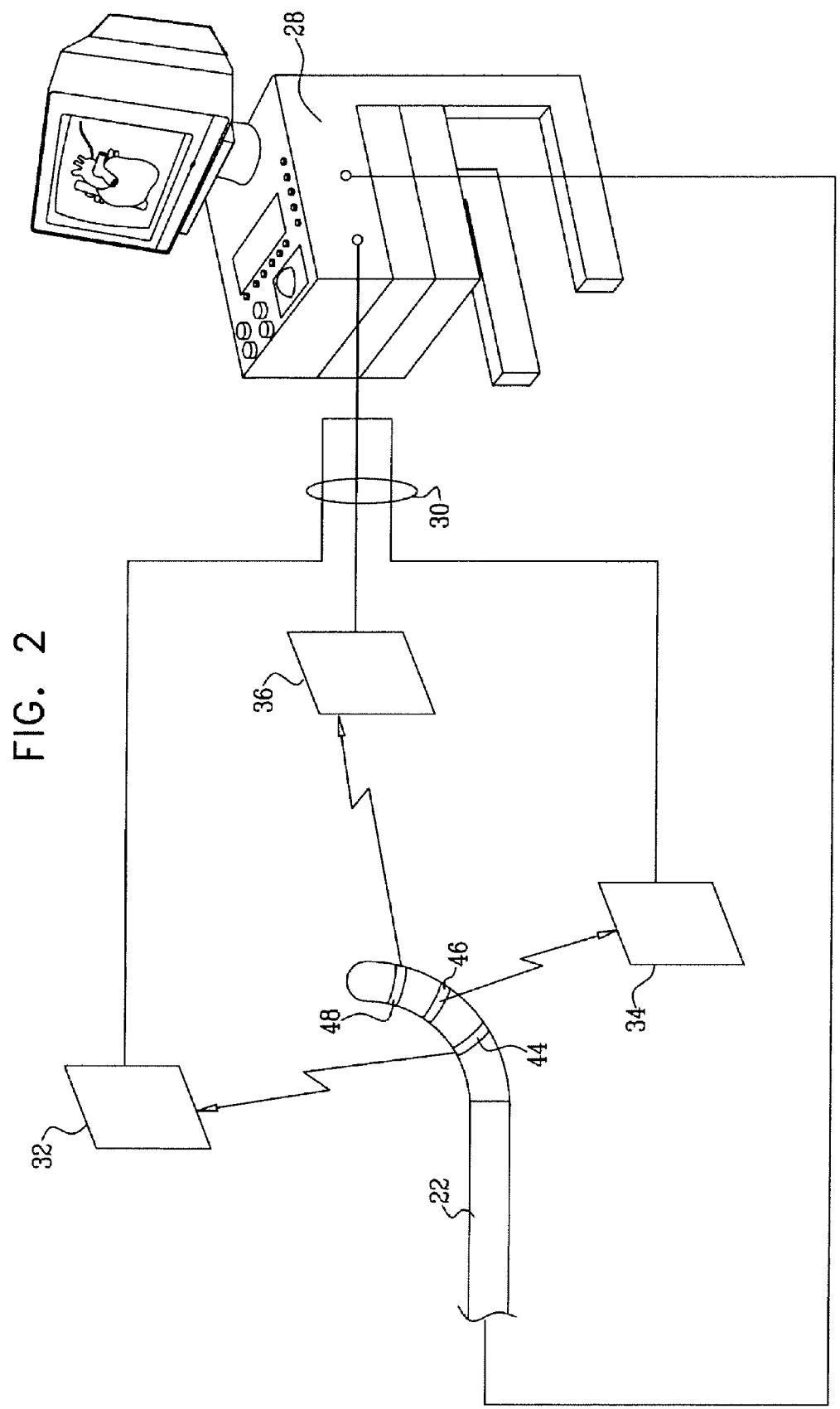
FIG. 2 is a detailed schematic view of a catheter in the system shown in FIG. 1, which is constructed and operative in accordance with a disclosed embodiment of the invention.

Reference is now made to FIG. 2, which is a detailed schematic view of the catheter 22 (FIG. 1), which is constructed and operative in accordance with a disclosed embodiment of the invention. Interaction is shown between electrodes 44, 46, 48 disposed on the catheter 22 and the patches 32, 34, 36. The electrodes 44, 46, 48 may be of any suitable shape and size, and may be used for other purposes, such as for electrophysiological sensing or ablation. In the pictured embodiment, each of the electrodes 44, 46, 48 communicates with one of the patches 32, 34, 36. The control unit 28 drives a current between each catheter electrode and the corresponding body surface electrode, and uses the current to measure the impedance between the two electrodes. Based on the measured impedances, the control unit 28 determines the catheter position relative to the body surface electrodes. Alternatively, greater or smaller numbers of electrodes may be used. For example, the control unit 28 may be set to multiplex the currents between one catheter electrode and multiple body surface electrodes. As another example, more than three body surface electrodes may be used for enhanced accuracy.

The system 20 is disclosed in further detail in the above-mentioned application Ser. No. 11/030,934. Although embodiments of the present invention are described herein with reference to this current-based measurement system, the principles of the present invention are equally applicable to other types of impedance-based position sensing systems, as well as to other types of position sensing systems, as are known in the art.

Figure 3:
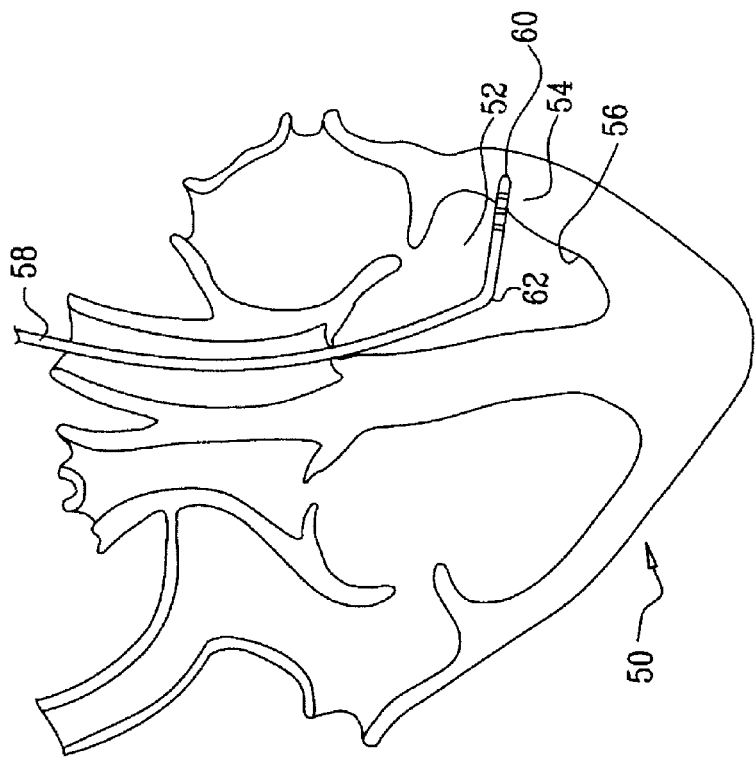
FIG. 3 shows schematic sectional views of a catheter being positioned in a left ventricle of a heart in accordance with a disclosed embodiment of the invention.
Figure 3:
Figure 3:
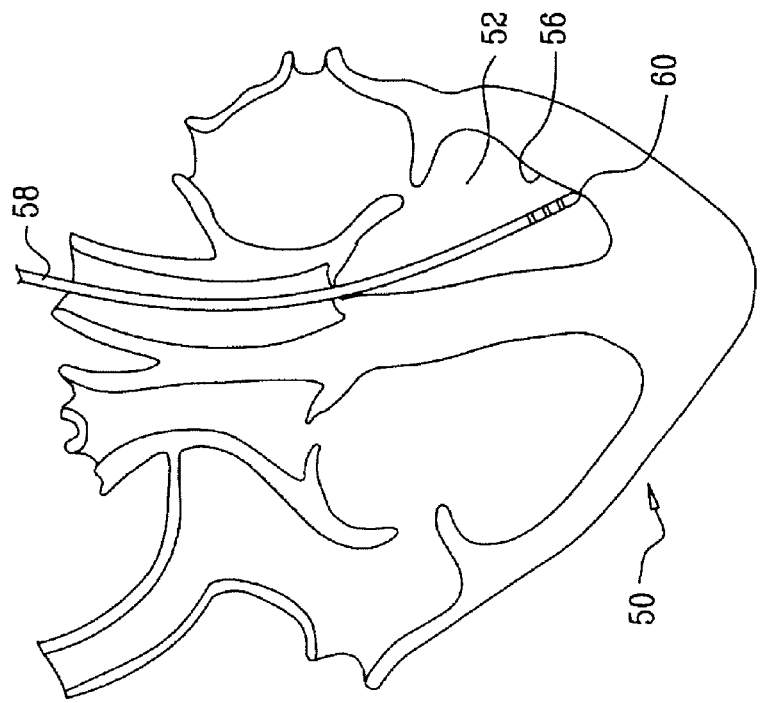

Reference is now made to FIG. 3, which shows a schematic sectional views of a heart 50, having a left ventricle 52, myocardium 54, and an endocardial surface 56. FIG. 3 illustrates a catheter 58 being positioned in the left ventricle 52 in accordance with a disclosed embodiment of the invention. A known difficulty with the position sensing technology as implemented in the system 20 (FIG. 1) is that impedance can suddenly change, due, for example, to a probe electrode coming in contact with inner body tissue. When such a sudden fluctuation occurs, the realtime image of the probe on the display 40 (FIG. 1) may appear to have an unrealistic shape or position. In the example of FIG. 3, the true position of the catheter 58 is indicated on the left side of FIG. 3. The catheter tip 60 is in contact with the endocardial surface 56 of the left ventricle 52. The apparent position of the catheter 58 is shown on the right side of FIG. 3, in which the tip 60 is shown to lie improbably deeply within the myocardium 54. The conformation of the distal portion of the catheter 58 also includes a sharp angulation 62, which would be unexpected in normal practice. The present invention provides for stabilizing the image of the catheter 58 in order to prevent unrealistic shapes or positions from appearing on a patient monitor.

Control Unit

Figure 4:
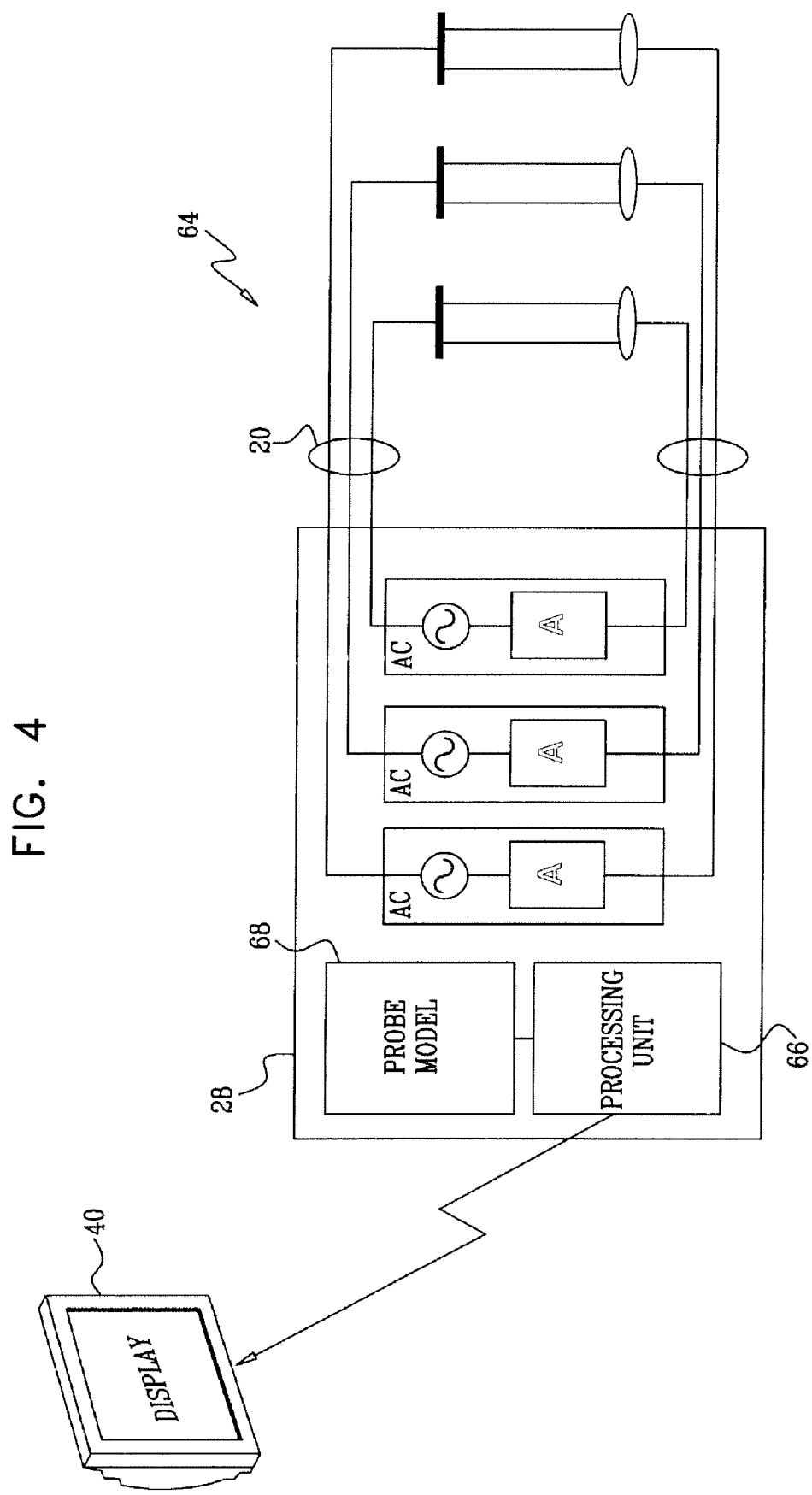
FIG. 4 is a detailed block diagram of a control unit in the system shown in FIG. 1, which is constructed and operative in accordance with a disclosed embodiment of the invention.

Reference is now made to FIG. 4, which is a detailed block diagram of the control unit 28 (FIG. 1), in accordance with a disclosed embodiment of the invention. The control unit 28 comprises circuitry 64 for driving currents and for measuring impedance. Each of a plurality of circuits drives a current through the catheter 20 (FIG. 1) in a closed loop consisting of a catheter electrode and a body surface electrode, as described more fully in the above-noted application Ser. No. 11/030, 934. Impedance readings are passed to a processing unit 66, which uses the readings to calculate the position coordinates of the catheter relative to the body surface electrodes. Based on these position coordinates, the processing unit 66 then generates realtime information. The processing unit 66 then compares the information to predictive information that is encoded in a probe model 68. Based on the comparison, the information is corrected as necessary in order to conform to the model's predictions and constraints. Alternatively, the information may be considered so erroneous that it must be disregarded entirely. In the first alternative, the information is used to generate an image that appears on the display 40.

Embodiment 1

With continued reference to FIG. 4, several methods are provided for stabilizing a probe image. In one aspect of the invention, the probe model 68 comprises a catalog of reasonable probe shapes. Typically, a probe, such as a catheter tip, is flexible, and can therefore assume a range of curved shapes. By maintaining a model of the realistic range of topologies, a matching algorithm can be used to force the probe image to assume a realistic shape, in accordance with the model topology. If the impedance reading determined for one of the electrodes does not match the one of the possibilities in the probe model 68, the reading is discarded or corrected. Thus, in the example of FIG. 3, in one alternative, the image on the right side of the figure would not be displayed. Alternatively, based on the probe model 68, a correction is applied, and the corrected image then appears on the display 40, as shown on the left side of FIG. 3.

Embodiment 2

Figure 5:
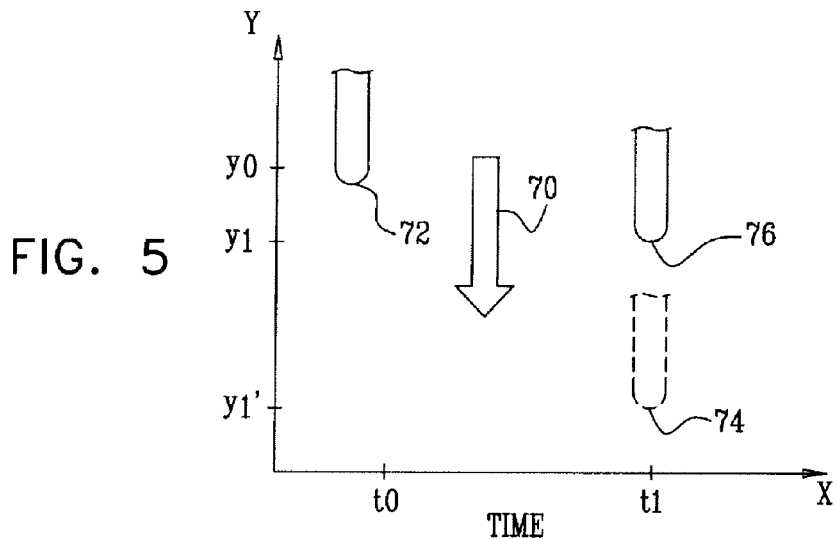
FIG. 5 schematically illustrates movements of a catheter being positioned in accordance with a disclosed embodiment of the invention.

A probe inside the body can be assumed to move no faster than a certain speed. If an impedance fluctuation causes an apparent movement that would exceed this maximum speed, the probe image can be constrained to a position bounded by the maximum speed. Reference is now made to FIG. 5, which schematically illustrates motion of a catheter being positioned in accordance with a disclosed embodiment of the invention. It is assumed that the catheter is positioned within a hollow body organ, is being detected using the impedance methodology described above, and is being viewed on a patient monitor. The catheter is being displaced in a downward direction indicated by an arrow 70. At a time $t_0$, the catheter is shown at a position 72, corresponding to $y_0$ on the y-axis. Subsequently, at time $t_1$, an apparent position 74 of the catheter, as detected by the impedance technique, is indicated by broken lines. In this embodiment, the probe model 68 includes possible movements of the catheter, and from the model, it can be deduced that the catheter could not have advanced farther than a position 76, corresponding to $y_1$. The catheter's position is then adjusted to have the coordinate $y_1$, which would be actually displayed on the monitor.

The models described in the foregoing embodiments may be combined to achieve the advantages of both speed and morphologic corrections.

Operation

Figure 6:
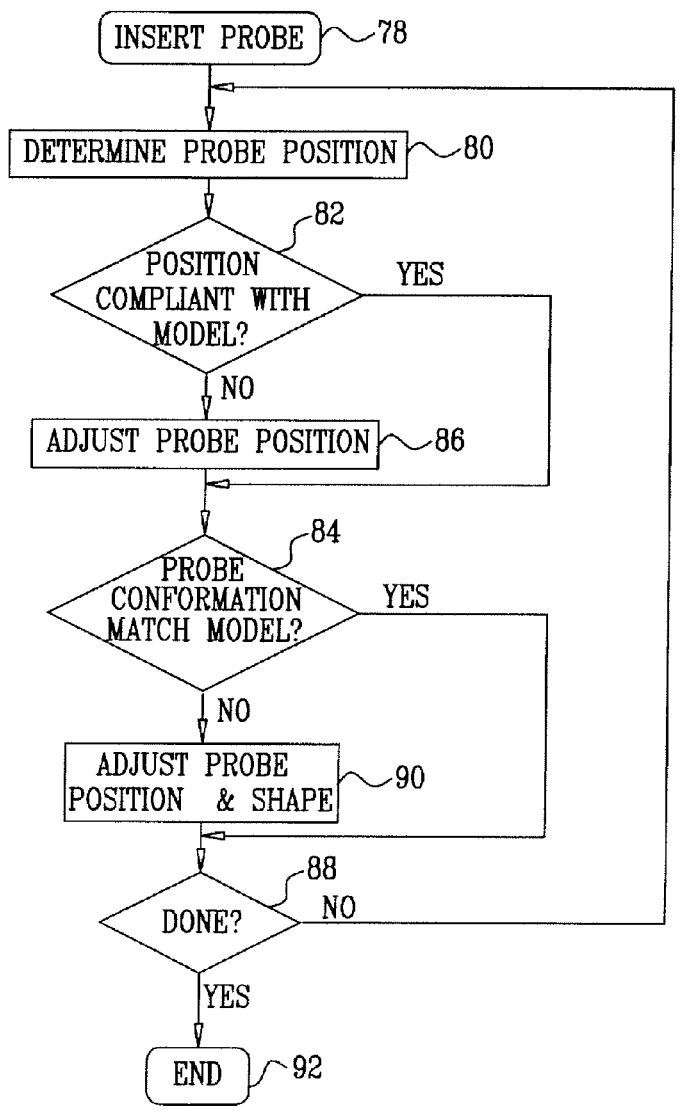
FIG. 6 is a flow chart of a method for correcting position measurements of a probe inside a living body in accordance with a disclosed embodiment of the invention.

Reference is now made to FIG. 6, which is a flow chart of a method for correcting position measurements of a probe inside a living body in accordance with a disclosed embodiment of the invention. At initial step 78, a probe is configured and inserted generally into an operational area of the body, for instance the left ventricle of a heart. An appropriate model, as explained above, describing possible conformations and movement limitations of the probe, is selected and loaded into a processing unit.

Next, a loop is executed iteratively, the actual iteration rate being related to the refresh rate of the display and the speed of the processing unit. At step 80 an apparent probe position, as measured by the system, is evaluated.

Control now proceeds to decision step 82, where it is determined if the current position of the probe as determined in step 80 complies with motion rate limitations encoded in the model introduced in initial step 78. This would be the case if the displacement of the probe from a previously determined position does not exceed permissible limitations during the time interval that has elapsed between the evaluation of the current and previous probe positions. If the determination at decision step 82 is affirmative, then control proceeds to decision step 84, which is described below.

If the determination at decision step 82 is negative, then control proceeds to step 86. An adjustment in the position of the probe is effected by the processing unit and displayed accordingly. The adjustment is generally in the opposite direction of movement, so that the displacement of the probe from its previously determined position does not exceed the limitation of the model.

Following performance of step 86, or if the determination at decision step 82 is negative, control proceeds to decision step 84, where it is determined if the present conformation of the probe corresponds to one of the possibilities encoded in the model.

If the determination at decision step 84 is affirmative, then control proceeds to decision step 88, which is described below.

If the determination at decision step 84 is negative, then control proceeds to step 90. Generally, when the probe fails to match one of the conformations in the model, an abrupt change in one or more impedance readings has occurred, often as a result of contact between the probe and the wall of the viscus being examined, e.g., the endocardium. Based on the model, a positional adjustment and a conformational adjustment of the probe are effected by the processing unit and displayed for the benefit of the operator, who never sees the impedance-related artifact. This is accomplished by an algorithm that measures topological distances between the apparent conformation of the probe and the possibilities encoded in the model. The possibility exhibiting a minimum distance is selected as the most likely true conformation of the probe. Associated with the possibility is a likely error in actual position of the probe, which is used for compensating the position of the probe on the display as well as adjusting its shape. For example, if an artifactual curvature would appear on the display, this would be corrected by the processing unit, so that the probe would appear as straight to the operator. An appropriate positional adjustment would also be displayed. Normally, the operator is alerted by a suitable indication that an automatic adjustment has been made by the processing unit. In some embodiments a Kalman filter may be employed in order to predict the true conformation and position of the probe.

For example, a geometric or topological model may be constructed, which would include the shape of a catheter and the distance of all its parts and features relative to a reference point. Then a known curve fitting procedure is applied to observed data points, e.g., least squares, nearest neighbors algorithm. Using the model, weak or noisy data points are supplemented by model predictions. Reliable data points, which would also agree with the model, are displayed directly.

Following performance of step 90, or if the determination at decision step 84 is affirmative, control proceeds to decision step 88, where it is determined if the medical procedure is complete. If the determination at decision step 88 is negative, then control returns to step 80, and another iteration of the loop begins.

If the determination at decision step 88 is affirmative, then control proceeds to final step 92. The probe is withdrawn, and the procedure terminates.

The process steps are shown above in a particular sequence in FIG. 6 for clarity of presentation. However, it will be understood that some of them can be performed in different orders. For example, it may be desirable to evaluate matches between the model of permissible probe conformations prior to evaluating motion displacements.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of determining a position of a probe that has been inserted into a body of a subject, comprising the steps of:
    providing a processing unit and a probe model;
    maintaining the probe model with a model of topologies comprising a range of shapes assumable by said probe;
    determining an apparent conformation of said probe in said body with the processing unit;
    using the processing unit and the probe model to establish that said apparent conformation is outside said range;
    using the processing unit to reference said probe model to determine a true conformation of said probe;
    using the processing unit to adjust said apparent conformation to said true conformation and
    displaying said true conformation.

2. The method according to 1, further comprising the step of adjusting an apparent position of said probe to a true position responsively to said step of referencing said model.

3. The method according to claim 2, wherein said apparent position is determined by measuring impedance between said probe and a plurality of locations that are remote from said probe.

4. The method according to claim 3, wherein measuring said impedance comprises performing the steps of:
    passing electrical currents through said body between at least one electrode disposed on said probe and said plurality of locations; and
    measuring respective characteristics of currents passing through said plurality of said locations.

5. The method according to claim 1, wherein said step of adjusting said apparent conformation is performed using a Kalman filter.

6. An apparatus for position sensing, comprising:
    a probe, comprising a plurality of probe electrodes, which is adapted to be inserted into a body of a subject;
    a plurality of body surface electrodes, which are adapted to be fixed to a surface of said body at respective locations;
    a display; and
    a controller comprising a processing unit configured to load and maintain a probe model and, the controller being adapted to be coupled to said probe and to said body surface electrodes so as to pass electrical currents through said body between said probe electrodes and said body surface electrodes, and adapted to determine position coordinates of said probe by measuring respective characteristics of said currents passing through said body surface electrodes, said controller being configured to:
    maintain the probe model having a model of topologies comprising a range of shapes assumable by said probe;
    determine an apparent conformation of said probe in said body with the processing unit;
    use the processing unit and the probe model to establish that said apparent conformation is outside said range;
    reference said probe model to determine a true conformation of said probe;
    use the processing unit to adjust said apparent conformation to said true conformation; and
    display said true conformation.

7. The apparatus according to claim 6, further comprising the step of adjusting an apparent position of said probe to a true position responsively to said step of referencing said model.

8. The apparatus according to claim 7, wherein said apparent position is determined by measuring impedance between said probe and said locations.

9. The apparatus according to claim 8, wherein measuring said impedance comprises measuring said respective characteristics of said electrical currents passing through said locations.

10. The apparatus according to claim 6, wherein said step of adjusting said apparent conformation is performed using a Kalman filter.

* * * * *